United States Patent [19]

Masurekar

[11] 4,275,164

[45] Jun. 23, 1981

[54] PROCESS AND NUTRIENT MEDIUM FOR GROWING MICROORGANISM

[75] Inventor: Prakash S. Masurekar, Webster, N.Y.

[73] Assignee: Eastman Kodak Company, Rochester, N.Y.

[21] Appl. No.: 91,216

[22] Filed: Nov. 5, 1979

[51] Int. Cl.$^3$ .......................... C12N 9/78; C12N 1/20
[52] U.S. Cl. .................................... 435/227; 435/253; 435/850
[58] Field of Search ............................... 435/227, 253

[56] References Cited

U.S. PATENT DOCUMENTS

| | | | |
|---|---|---|---|
| 3,806,420 | 4/1974 | Holz et al. | 435/816 X |
| 3,907,644 | 9/1975 | Mollering et al. | 435/227 X |
| 4,039,384 | 8/1977 | Suzuki et al. | 435/227 |
| 4,087,329 | 5/1978 | Terada et al. | 435/227 |

OTHER PUBLICATIONS

Smulmajster, Journal of Bacteriology, vol. 75, pp. 633–639 (1958).
Szulmajster, Biochem. Biophys. Acta, vol. 30, pp. 154–163 (1958).

*Primary Examiner*—Lionel M. Shapiro
*Attorney, Agent, or Firm*—J. Jeffrey Hawley

[57] ABSTRACT

A fermentation process and improved aqueous nutrient medium is used for the production of urease-free creatinine iminohydrolase from an aerobic soil microorganism. In the process, a fresh sample of the microorganism grown on a creatinine-containing maintenance medium is transferred to a microbial growth medium to grow the microorganism, the growing microorganism is then transferred to a production medium to produce microorganism in which creatinine iminohydrolase production has been induced, and the desired enzyme is then extracted from the microorganism. An improved aqueous nutrient medium for use as the aforementioned production medium is disclosed.

17 Claims, No Drawings

PROCESS AND NUTRIENT MEDIUM FOR GROWING MICROORGANISM

FIELD OF THE INVENTION

The present invention relates to a process and an improved aqueous nutrient medium for growing an aerobic soil microorganism which produces urease-free creatinine iminohydrolase.

BACKGROUND OF THE INVENTION AND RELATED APPLICATIONS

Creatinine iminohydrolase is an enzyme which specifically hydrolyzes creatinine to ammonia. Accordingly, by contacting an aqueous liquid containing creatinine with this enzyme to generate ammonia, the presence and/or concentration of creatinine in the liquid can be determined by detecting the level of generated ammonia. This enzyme can therefore play an important role in the clinical laboratory where it can be used as a diagnostic test reagent for the determination of creatinine in biological liquids.

Creatinine iminohydrolase, sometimes referred to as creatinine desimidase, has been obtained from various microorganisms. For example, J. Szulmajster in *J. Bacteriolol*, 75: 633 (1958) and in *Biochim Biophys Acta*, 30: 154 (1958) describes a preparation of creatinine iminohydrolase obtained from the anaerobic, gram-positive microorganism *Clostridium paraputrificum*. A method of growing the *Clostridium paraputrificum* microorganism is also described in these Szulmajster publications. However, these publications relate specifically to an anaerobic, gram-positive microorganism, and the disclosed fermentation method for growing the microorganism requires a long time. Moreover, the amount of microbial cells grown and the yield of enzyme extracted therefrom is relatively small. Accordingly, as of the filing date of the present specification, large-scale production of enzyme from the microbial source *Clostridium paraputrificum* does not appear to be practical.

U.S. Pat. Nos. 4,087,329 and 4,134,793 describe the production of the enzyme creatinine desimidase from one of several aerobic microbial sources including microorganisms of the genera Brevibacterium, Corynebacterium, Pseudomonas, and Arthrobacter. These patents further describe a nutrient medium which may be used for culturing microorganisms of the aforementioned genera. These patents assert that the formulation of this nutrient medium can be widely varied and can contain any of a large number of specifically recited carbon and nitrogen sources, as well as other optional nutrients including inorganic materials, a creatinine inducer, and the like.

Goodhue, Esders, and Masurekar copending U.S. Patent Application Ser. No. 091,218, filed concurrently herewith and entitled "Creatinine Iminohydrolase Free From Urease Activity" describes and claims a new creatinine iminohydrolase enzyme preparation free from urease activity obtained from an aerobic soil microorganism, preferably the aerobic soil microorganism ATCC 31546. Because this enzyme preparation is free of urease contamination and is highly specific for creatinine, creatinine assays can be performed with this enzyme without regard to interference by urea and other nitrogenous substances that are often present in biological aqueous liquids to be assayed for creatinine, e.g., serum. The new urease-free creatinine iminohydrolase enzyme preparation described by Goodhue, Esders, and Masurekar in the aforementioned patent application is therefore highly desirable.

An improved process and aqueous nutrient medium for growing a creatinine iminohydrolase-producing aerobic soil microorganism and increasing the yield of the creatinine iminohydrolase from the microorganism would represent a clearly advantageous addition to the art. Such a process and medium would be particularly desirable if useful with the aerobic soil microorganism ATCC 31546 noted above.

McCollough, Esders and Lynn, U.S. Patent Application Ser. No. 091,217 filed concurrently herewith entitled "Process For The Recovery Of Intracellular Enzymes" describes and claims an improved method for the extraction of intracellular enzymes such as urease-free creatinine iminohydrolase from an aerobic soil microorganism. The foregoing Goodhue, Esders and Masurekar and McCollough, Esders and Lynn copending patent pulications are incorporated by reference herein.

SUMMARY OF THE INVENTION

The present invention provides an improved fermentation process and improved aqueous nutrient medium for growing under aerobic conditions an aerobic soil microorganism from which a creatinine iminohydrolase enzyme preparation can be obtained.

In one embodiment, the invention provides a fermentation process for production, especially large-scale production, of creatinine iminohydrolase from an aerobic soil microorganism maintained on an aqueous maintenance medium containing creatinine under aerobic conditions at a pH of from about 5.0 to 10.0. This fermentation process comprises the steps of (a) transferring a fresh sample of the aforementioned microorganism from the maintenance medium to a microbial growth medium having a pH of from about 5.0 to 10.0 to grow the microorganism aerobically, microbial growth medium comprising an aqueous nutrient medium, substantially free from creatinine, containing nutrients including a vegetable or non-peptic milk protein hydrolysate effective under aerobic conditions to grow the microorganism;

(b) transferring the microbiol growth medium containing the growth microorganism of step (a) to a production medium having a pH in the range of from about 5.0 to 10.0 to produce under aerobic conditions a microorganism in which creatinine iminohydrolase production has been induced; and (c) extracting urease-free creatinine iminohydrolase from the microorganism produced in step (b).

The production medium described in step (b) above comprises an aqueous nutrient medium containing components (i)–(iv) as follows:

(i) a carbon source comprising glucose or an amino acid precursor representing an organic acid free from amino groups, or preferably both glucose and the amino acid precursor, (ii) a nitrogen source comprising creatinine and preferably also containing a vegetabie protein hydrolysate or a non-peptic milk protein hydrolysate or a mixture of vegetable protein hydrolysate and non-peptic milk protein hydrolysate, (iii) trace nutrients, and (iv) a buffer.

In a preferred embodiment, the improved fermentation process and improved aqueous nutrient medium of the invention have been found useful for production of urease-free creatinine iminohydrolase from an aerobic soil microorganism such as ATCC 31546. The term "urease-free" as defined herein refers to an enzyme preparation that in crude, unpurified form as extracted and separated from the microbial cells in which it was produced exhibits substantially no urease activity. A typical assay procedure for determining urease activity can be carried out using the "GDH" assay method of Procedure 5 hereinafter wherein urea is substituted for creatinine.

DESCRIPTION OF THE PREFERRED EMBODIMENTS

The process of the present invention provides an improved aqueous nutrient medium for the growth of an aerobic soil microorganism, preferably the microorganism ATCC 31546, from which increased yields of creatinine iminohydrolase can be obtained. The microorganism identified as ATCC 31546 has received this designation based on its deposit with the American Type Culture Collection, Rockville, Maryland, 20852 U.S.A. This microorganism has been tentatively assigned to the genus Flavobacterium and given the species name *filamentosum*. The present invention can also be employed with creatinine iminohydrolase-producing aerobic soil microorganisms other than ATCC 31546. For example, the invention can advantageously be used to produce creatinine iminohydrolase from aerobic soil microorganisms of the genera noted in U.S. Pat. Nos. 4,087,329 and 4,134,793 previously referenced herein.

The fermentation process described hereinabove facilitates good growth of the microorganism and significantly improves yield of the enzyme. Unexpectedly, these high advantageous results are achieved in the process by growing the microorganism in a nonspecific microbial growth medium featuring nutrients, substantially free from creatinine, comprising a vegetable or non-peptic milk protein hydrolysate and then inducing enzyme formation in a production medium featuring a well-defined carbon source and a nitrogen source including creatinine.

In one preferred embodiment, an improved aqueous nutrient medium containing at least one "direct" amino acid precursor, as defined hereinafter, can be employed as the production medium in the invention to provide high yields of creatinine iminohydrolase in excess of 500 units per liter of medium. In an especially preferred embodiment wherein the improved aqueous nutrient contains a mixture of glucose and at least one direct amino acid precursor, the invention provides even higher yields of creatinine iminohydrolase production in excess of 650 units per liter.

Production Medium

In the course of formulating the production medium comprising an aqueous nutrient medium having components (i)-(iv) described in the "Summary of the Invention", various conventional carbon sources for microorganisms were investigated. As demonstrated in the appended examples, a number of conventional carbon sources used to grow microorganisms identified in U.S. Pat. Nos. 4,087,329 and 4,134,793 as capable of producing creatinine iminohydrolase are of little or no value for producing creatinine iminohydrolase from aerobic microorganisms such as ATCC 31546. For example, carbon sources such as glycerol, sucrose, acetic acid, aspartic acid, glutamic acid, and glycine produce microbial cells yielding only small amounts of creatinine iminohydrolase. Certain of the foregoing carbon sources identified as being of little or no value in the present method provide good cell growth of the microorganism, but the resultant microorganism yields little or none of the desired creatinine iminohydrolase enzyme.

Those carbon sources which have been found useful include glucose and amino acid precursors representing organic acids free from amino groups. Amino acid precursors refer herein to both "direct" and "indirect" precursors for amino acids. A direct precursor represents a substance which is one metabolic reaction step removed from an amino acid, whereas as indirect precursor requires two metabolic reaction steps to form an amino acid. Thus, for example, fumaric acid represents a "direct" amino acid precursor as it can be metabolically converted to the amino acid aspartic acid in a single reaction step; whereas lactic acid represents an "indirect" amino acid precursor as it must first be metabolically converted to pyruvic acid (a direct amino acid precursor) which can then be metabolically converted to alanine. In the present invention, direct amino acid precursors are generally preferred over indirect amino acid precursors.

The amino acid precursors employed in the aqueous nutrient medium of the production medium are further characterized as organic acids free from amino groups. A partial listing of preferred such organic acids which are direct amino acid precursors includes fumaric acid, $\alpha$-ketoglutaric acid, and pyruvic acid. A partial listing of useful such organic acids which are indirect amino acid precursors includes malic acid, lactic acid, citric acid, and succinic acid.

The amount of the glucose or the above-described amino acid precursor employed as a carbon source can vary. Useful amounts have typically been found to be in the range of from about 1.0 to 20.0 grams per liter of the aqueous nutrient medium, preferably in the range of from about 5.0 to 10.0 grams per liter.

An especially preferred embodiment of the invention provides an improved aqueous nutrient medium as the production medium and contains a carbon source comprising both glucose and one or more of the amino acid precursors. This embodiment can substantially increase the yield of creatinine iminohydrolase enzyme from the microorganism. In this embodiment, the total amount of the glucose and the above-described amino acid precursor is typically within the 5.0 to 10.0 g/l range specified above with the weight ratio of glucose to the amino acid precursor typically being within the range of from about 1:10 to 1:1.

The nitrogen source employed in the aqueous nutrient medium of the production medium need comprise only creatinine. However, a preferred aqueous nutrient medium of the invention which can be employed as the production medium comprises both creatinine and a vegetable protein hydrolysate or a non-peptic milk protein hydrolysate. Among the vegetable and non-peptic milk protein hydrolysates which can be employed in this preferred embodiment are tryptone; soy protein hydrolysates such as Hy-Soy, a tradename of Scheffield Chemical Division of Kraftco Corporation, Union, New Jersey; tryptic casein hydrolysates such as Trypticase Peptone available from Bioquest (BBL), Cockeysville, Maryland; protease casein hydrolysates and the like. Peptic milk protein hydrolysates, i.e., milk protein hydrolyzed by pepsin, have generally been found to provide low rates of microbiol cell growth and low rates of microbial enzyme production.

The amount of creatinine which has been found useful typically is within the range of from about 0.5 to about 20.0 grams per liter of the aqueous nutrient medium employed as the production medium, preferably from about 4.0 to 12.0 grams per liter. The amount of vegetable and/or non-peptic milk protein hydrolysate which has been found useful typically is within the range of from about 1.0 to 10.0 grams per liter, preferably about 1.0 to 5.0 grams per liter.

The trace nutrients contained in the aqueous medium representing the production medium includes water-soluble inorganic salts. Yeast extract can also be present. Typically these trace nutrients are added in small quantities in an amount effective to promote cell growth of the microorganism and increased yield of enzyme from the microorganism. Typically, a useful amount of yeast extract is within the range of from about 0.1 gram to about 2 grams per liter of the medium, preferably from about 0.5 to about 1.5 grams per liter. Vitamins can also be present as optional trace nutrients.

Typical water-soluble inorganic salts which can be present as trace nutrients include water-soluble salts of phosphorus, magnesium, calcium, iron, zinc, sodium, and other water-soluble salts, the cationic component thereof typically being selected from Periods 3 and 4 of the Periodic Table of the Elements. Preferably, a mixture of several different inorganic salts are present as trace nutrients. One inorganic salt mixture which has been found especially useful is an aqueous 0.1 N HCl solution of the following composition, the concentration of each listed component based on the amount present in one liter of aqueous solution:

$MgSO_4.7H_2O$—12.2 g
$CaCl_2.2H_2O$—0.076 g
$FeSO_4.7H_2O$—2.8 g
$MnSO_4.H_2O$—1.7 g
$ZnSO_4.7H_2O$—0.06 g
NaCl—0.6 g
$NaMoO_4.2H_2O$—0.1 g

The aqueous nutrient medium representing the production medium also contains a buffer. Preferably, the buffer is a phosphorous-containing buffer such as a phosphate buffer, although other buffers may also be used. In this preferred case, the buffer not only serves as a buffer but also serves as a trace phosphorous source for the microorganism. A preferred phosphate buffer is dipotassium hydrogen phosphate, $K_2HPO_4$, typically present in an amount within the range of from about 3.0 to 10.0 grams per liter, preferably about 3.0 to 6.0 grams per liter.

The pH of the aqueous nutrient medium representing the production medium is typically in a range of from about 5.0 to 10.0, preferably about 6.0 to 7.5. The pH of the medium can readily be adjusted to a value in the aforementioned range by addition of a base such as KOH or NaOH, preferably NaOH. The pH is then maintained within this range by the presence of the above-noted buffer.

The production medium can also contain other optional components as will be appreciated by those skilled in the art. Because foaming is often encountered when growing microorganisms in a large-scale fermentor, foam control agents can be included in the medium. One such foam control agent which can be employed is a polyglycol such as Polyglycol P-2000, a tradename of Dow Chemical Company, Midland, Michigan. Typically, when used, this foam control agent is employed in an amount up to about 0.5 grams per liter although lower amounts of 0.1 grams per liter have generally been found sufficient to control foaming. Other foam control agents can also be used; the main criterion for selection being minimal or no inhibition of microbial growth and enzyme synthesis at a concentration level that will control the foam.

Fermentation Process For Enzyme Production

As explained in the "Summary of the Invention", the above-described production medium is advantageously employed in the final step of a fermentation process suitable for large-scale production of creatinine iminohydrolase from an aerobic soil microorganism such as the microorganism ATCC 31546.

This fermentation process employs a sample of the microorganism grown on a maintenance medium under aerobic conditions at pH conditions similar to those described above for the production medium. Thus, the pH is typically adjusted from about 5.0 to 10.0, preferably about 6.0 to 7.5, by addition of base, preferably NaOH or KOH, although other bases may also be employed. The temperature of the maintenance medium is typically within the range of from about 15° to 42° C., preferably about 25° to 30° C.

The maintenance medium typically comprises an aqueous medium including a nitrogen source comprising creatinine; a carbon source preferably including one or more of the above-described amino acid precursors representing an organic acid free from amino groups; trace nutrients such as one or more water-soluble inorganic salts and optionally yeast extract; and buffer. If desired, other conventional culture materials such as agar and the like can also be present.

A maintenance medium which has been found especially useful has the following composition, the concentration of each listed component based on the amount present in one liter of the maintenance medium:

Agar—20.0 g
Fumaric acid (carbon source)—10.0 g
Creatinine (nitrogen source)—5.0 g
$K_2HPO_4$ as buffer (anhydrous)—5.0 g
Yeast extract—1.0 g
Salt solution—10.0 ml
Distilled water—800.0 ml
pH adjusted to 6.7 with NaOH and volume made up to 1 liter with distilled water.

The salt solution noted immediately hereinabove is a 0.1 N HCl aqueous solution and has the following composition, the concentration of each listed component based on the amount present in one liter of salt solution:

$MgSO_4.7H_2O$—12.2 g
$CaCl_2.2H_2O$—0.076 g
$FeSO_4.7H_2O$ —2.8 g
$MnSO_4.H_2O$—1.7 g
$ZnSO_4.7H_2O$—0.06 g
NaCl—0.6 g
$NaMoO_4. 2H_2O$—0.1 g

The fermentation process is initiated in step (a) wherein a "fresh" sample of the microorganism is transferred to a microbial growth medium to grow the microorganism. The term "fresh" sample of microorganism refers to a sample of the microorganism which has been incubated and maintained in the maintenance medium at about 25° C. for a relatively short duration, typically on the order of from about 24 to 72 hours, preferably about 48 hours. A sample of a microorganism which has been maintained and incubated in the maintenance medium for longer periods of time has typically been found less useful than a fresh sample of a microorganism.

To provide a ready supply of fresh sample of microorganism obtained from the maintenance medium, one can store the microorganism as a freeze-dried powder at temperatures in the range of from about 4° to 25° C., thereby suspending cellular growth processes of the microorganism. New cultures of the freeze-dried powder in the above-described maintenance medium can then be periodically initiated as desired. In this way, one can provide a continual supply of "fresh" sample of the microorganism for transfer to the microbial growth medium in step (a) of the fermentation.

Alternatively, one can also provide a supply of fresh sample of microorganism by storing it frozen in liquid nitrogen as described in the appended Procedures.

The composition of the microbial growth medium in step (a) of the fermentation process, although important, can vary widely. In general, the microbial growth medium is selected to achieve maximal cell growth of the microorganism consistent with good yields of enzyme production in steps (b) and (c) of the process. This is achieved by employing certain conventional non-specific nutrient media as the microbial growth medium in step (a), even though a well-defined carbon source and specific nitrogen source are employed in the production medium of step (b) of the process. The beneficial results produced by the use of step (a) together with step (b) were not expected and could not have been predicted. That is, one skilled in the art could not have predicted that a microorganism which produces enzyme non-constitutively (i.e., microorganisms in which production of the desired enzyme is achieved by growth in a medium including the substrate or substrate analog for the desired enzyme) would produce optimum yields of enzyme without use of a specifically formulated, well-defined nutrient medium throughout the fermentation process. Unexpectedly, therefore, the present fermentation process for aerobic soil microorganisms such as ATCC 31546 was found to provide improved results using creatinine as a nutrient in both the maintenance and production media but without creatinine in the microbial growth medium in step (a) of the process.

The foregoing characteristic is quite advantageous. This allows one to formulate the microbial growth medium from certain non-specific, commercially available, pre-formulated nutrient media commonly referred to in the art as "complex" media. These "complex" media are so named because they include a complex mixture of microbial nutrients typically derived from a vegetable, milk, meat or fish source. Thus, the media typically contain a vegetable, milk, fish, or meat protein as a nitrogen source and a variety of other inorganic salt and vitamin nutrients extracted from the source. Supplemental carbon sources such as a sugar as well as other supplemental vitamin and mineral nutrients may also be present in these complex media. Those complex media which provide good results as a microbial growth medium in the present invention are media derived from a vegetable or milk source and which contain a vegetable protein hydrolysate or a non-peptic milk protein hydrolysate.

Thus, the principal properties of the microbial growth medium are that the medium be substantially free from creatinine and contain nutrients including a vegetable and/or a non-peptic milk protein hydrolysate.

The pH conditions of the microbial growth medium are similar to those used for the maintenance medium. Typically, a pH in the desired range can be obtained by use of a nonspecific nutrient medium as described above without addition of a separate buffer or a separate base. For example, in the case of the so-called "complex" media noted above, the manufacturer of the complex media often incorporates a buffer into the media during its preparation to maintain the media in the preferred pH range of about 6.0 to 7.5.

The temperature conditions for the microorganism in the growth medium can vary. Typically, good cell growth in the growth medium in step (a) of the process occurs over a temperature range of from about 20° to 37° C., preferably about 25° to 30° C.

The sample of microorganism which is transferred in step (a) of the fermentation process to the microbial growth medium is incubated in this growth medium for a period effective to obtain maximal cell growth of the microorganism without causing lysis (i.e., rupture) of the microbial cells. The effective time period for this can vary depending upon the composition of the medium as well as the number of cells transferred to the growth medium. In the case of a preferred microbial growth medium composed of a vegetable protein hydrolysate such as Tryp-Soy Broth, available from Scott Laboratories, Inc., Fiskeville, R.I., the effective incubation period for a sample of the microorganism obtained from the maintenance medium and inoculated into a flask containing 25 ml of the microbial growth medium is about 5 to 11 hours, preferably about 7 to 9 hours.

During step (a) sufficient oxygen to maximize cell growth of the microorganism should be supplied. In general, the optimum amount of oxygen can readily be determined by monitoring cell growth at several different air oxygen flow rates and agitation rates (of the medium) for a given volume of microbial growth medium and selecting an air flow rate and agitation rate at or above that at which cell growth is maximized.

Having grown the microorganism in step (a) of the fermentation process, the microbial growth medium containing the growing cells is transferred in step (b) to the production medium. In step (b), the microbial growth medium containing growing cells is typically transferred, in total, to the production medium. This microbial growth culture (i.e., the microbial growth medium and the growing cells contained therein) thus serves as an inoculum for the production medium.

The production medium is contained in a fermentor. Such a fermentor has a capacity of at least 25 liters, typically 150 liters to 200,000 liters. Depending upon the size of the final production fermentor, the preparation of the microbial growth medium containing the growing cells which occurs in step (a) of the process can be carried out in stages to obtain a sufficient quantity of microbial growth culture to serve as the inoculum for the final production fermentor.

For instance, in the case where the final production fermentor has a volume of approximately 150 liters, step (a) is advantageously carried out in two stages as described in detail in the appended examples. Typically, in each stage of step (a) the cell growth of the microorganism in the microbial growth medium is maximized and the resultant culture (containing both the medium and growing cells) is used as an inoculum for a succeeding stage of step (a) in which the culture is introduced into a new, generally larger batch of microbial growth medium.

Where the final production-scale fermentor is larger than 150 liters, step (a) can be carried out in more than two stages to obtain a sufficient quantity of microbial growth culture for introduction into the final production-scale fermentor in step (b) of the fermentation process. Typically, the volume of microbial growth culture produced in the last stage of step (a) to the volume of production medium employed in step (b) is within the range of from about 1:50 to 1:5.

The composition of the production medium employed in the present fermentation process is as described in the "Production Medium" section of this specification. Likewise, the pH conditions maintained during incubation of the microorganism in the production medium are identical to those described in the "Production Medium" section. Sufficient oxygen to maintain maximum enzyme production by the microorganism is also important. This can readily be determined by monitoring the amount of enzyme extracted in step (c) of the fermentation process from a given volume of production medium as the oxygen or air flow rate as well as the agitation rate of the medium is varied over a range of values in step (b) of the process. One then selects an oxygen or air flow rate and agitation rate at or above that for which the amount of enzyme produced is maximized. The incubation time for the microorganism in step (b) of the fermentation process will vary depending on the specific composition of the production medium, the oxygen transport rate, temperature, and other conditions. Typical incubation times for a 150 liter production scale fermentor are within the range of from about 10 to 14 hours. As described above, if necessary or desirable, anti-foam agents can be added to the production medium, or they can be added at an earlier stage of the fermentation multi-stage process to the microbial growth medium.

An aerobic soil microorganism such as ATCC 31546 grown in the production medium of the present fermentation process can generally be grown over a reasonable range of temperatures to produce good yields of creatinine iminohydrolase enzyme. Good results can be obtained in a temperature range of from about 20° to 37° C. Best results have typically been achieved at a temperature of about 25° to 30° C.

Following completion of step (b), the desired urease-free creatinine iminohydrolase enzyme is recovered from the microbial cells in step (c). This can be accomplished by conventional means whereby the cells are disrupted by sonication, grinding, or the like; and the desired enzyme preparation is separated from the medium by organic solvent fractional precipitation or other conventional enzyme separation and purification techniques. An especially preferred method for recovering the desired enzyme and to obtain increased enzyme yield is described in McCollough, Esders and Lynn, U.S. patent application Ser. No. 091,217, filed concurrently herewith and entitled "Process for Recovery of Intracellular Enzymes".

The following, non-limiting examples are provided to further illustrate the invention. In the examples, the following materials were used:

Materials

1. Microorganism—the aerobic soil microorganism ATCC 31546
2. Medium No. 1
   Agar—20.0 g/l
   Fumaric acid (carbon Source)—10.0 g/l
   Creatinine (nitrogen source)—5.0 g/l
   $K_2HPO_4$ (anhydrous)—5.0 g/l
   Yeast extract—1.0 g/l
   Modified salt solution C—10.0 ml
   Distilled Water—800.0 ml
pH was adjusted to 6.7 with KOH, and made up to 1 liter with distilled water.
   Composition of modified salt solution C:
   $MgSO_4.7H_2O$—12.2 g/l
   $CaCl_2.2H_2O$—0.076 g/l
   $FeSO_2.7H_2O$—2.8 g/l
   $MnSO_4.H_2O$—1.7 g/l
   $ZnSo_4.7H_2O$—0.06 g/l
   NaCl—0.6 g/l
   $NaMoO_4.2H_2O$—0.1 g/l
Made up to 1 liter with 0.1 N HCl.
3. Medium No. 2 had the same composition as Medium No. 1, except that no agar was added.
4. Medium No. 3 had the same composition as Medium No. 2, except that 0.1 g of a polyglycol, Polyglycol P-2000 (a tradename of Dow Chemical Co., Midland, MI) per liter was added.
5. Medium No. 4—Medium for Testing Culture Purity
   Glucose—10.0 g/l
   Yeast extract—10.0 g/l
   Potassium phosphate (dibasic)—1.0 g/l
   Salt solution A-1—2.0 ml/l
   Salt solution A-2—2.0 ml/l
   Agar—20.0 g/l
pH was adjusted to 7.0 and made up to 1 liter with distilled water.
   Salt solution A-1:
   $MgSO_4.7H_2O$—100.0 g/l
   $FeSO_4.7H_2O$—10.0 g/l
   $MnSO_4.H_2O$—1.0 g/l
   $NaMoO_4.2H_2O$—0.5 g/l
Made up to 1 liter in 0.1 N HCl.
   Salt solution A-2:
   $CaCl_2$—10.0 g/l
   Distilled water—to 1.0 liter
6. Chemicals: Yeast extract was a product of Difco Laboratories (Detroit, MI); agar was obtained from Medox Chemical Ltd (Ottawa, Ontario, Canada); L-glutamic dehydrogenase; tris(hydroxymethyl)aminomethane buffer (tris), N,N-bis(2-hydroxyethyl)glycine (bicine), egg white lysozyme, nicotinamide adenine dinucleotide phosphate, reduced form (NADPH), ribonuclease and deoxyribonuclease from bovine pancreas were obtained from Sigma Chemical Co. (St. Louis, MO). Eastman Organic Chemicals (Rochester, NY) was the supplier of organic chemicals. All other chemicals were analytical grade and were obtained from commercial sources.

In the examples, the following procedures were used:

Procedures

1. Culture Preservation and Maintenance

A culture of the microorganism ATCC 31546 was preserved by growing the culture for ten hours at 30° C. in Tryp-Soy Broth, a "complex" medium composed of a vegetable protein hydrolysate sold by Scott Laboratories Inc. Fiskeville, RI. The cells were then separated aseptically and resuspended in sterile 10% aqueous glycerol with Allen's salt solution (Allen, M. B., Archives of Mikrobiology, Vol. 32, p. 270–277 (1959). A small volume, 0.5–2.0 ml of this culture was added to a sterile glass ampoule which was then sealed and stored in liquid nitrogen. To obtain a sample of the microorganism, the culture in the ampoule was thawed and the contents were aseptically transferred to Tryp-Soy Broth and grown for 10 hours at 30° C. A loopful of this culture was transferred aseptically to slants of Medium No. 1 incubated at 30° C.

2. Small-scale Enzyme Production

Small-scale enzyme production was achieved as follows:

A fresh sample of culture grown for two days on Medium No. 1 slants as described in Procedure 1 above was obtained. From this slant, a loopful of culture was inoculated into 25 ml of a microbial growth medium of the type employed in the present invention contained in a 250 ml Erlenmeyer flask. The microbial growth medium employed consisted of Tryp-Soy Broth, referred to hereinabove. Following inoculation of the culture into the Erlenmeyer flask, the flask was shaken at 200 rpm at 30° C. for eight hours to produce good cellular growth without lysis of the microbial cells. Thereafter, a sample of the contents of the flask was microscopically inspected for culture purity and then aseptically centrifuged at 15,000 xg in a refrigerated centrifuge (available from DuPont Instruments, Newton, CT) for 15 minutes to separate the cells from the Tryp-Soy Broth. The supernatant containing the Tryp-Soy Broth was discarded, and the solid material containing the precipitated microbial cells was then re-suspended in a volume of sterile distilled water equal to that present before centrifugation. 2 ml of this latter suspension was then used as an inoculum for a 250 ml Erlenmeyer flask containing 25 ml of a production medium to obtain further cell growth and to promote enzyme production by the microorganism. The specific composition of the production medium was varied as described in the following examples. However, in each case, once the microorganism was transferred as a 2-ml inoculum to the flask containing the particular production medium of interest, the flask was shaken at 30° C., 200 rpm for 10 hours. Thereafter, samples of the culture were withdrawn, diluted and dry-cell weight was determined. In addition, a 2.5 ml aliquot of the culture was centrifuged at 15,000 xg in a refrigerated centrifuge to separate the cells from the production medium. The supernatant containing the production medium was discarded. The precipitated cells were disrupted as in Procedure 4 below, and enzyme activity was assayed as described in Procedure 5 below.

3. Large-scale Enzyme Production

Large-scale enzyme production was carried out using a 150-liter fermentor as follows:

First, following the same steps described in Procedure 2 above, a fresh sample of the microorganism ATCC 31546 culture which had been grown for two days on Medium No. 1 slants was transferred into 25 ml of microbial growth medium contained in a 250-ml Erlenmeyer flask. The microbial growth medium was the same as that described in Procedure 2 above. The first stage of inoculum growth in the microbial growth medium was carried out by shaking the flask at 200 rpm, 25° C. for 12 hours. A sample of the contents of the flask was thereafter microscopically inspected for culture purity. Thereafter, in the second stage of inoculum growth in the microbial growth medium, the contents of two 250-ml Erlenmeyer flasks containing first-stage culture were transferred aseptically to a 14-liter fermentor containing 10 liters of sterilized microbial growth medium having the composition described in Procedure 2 above and also containing 0.01 wt% of a polyglycol anti-foam agent sold under the tradename Polyglycol P-2000 by Dow Chemicals, Midland, MI. In the second stage of inoculum growth, the 14-liter fermentor was agitated at 1300 rpm while maintaining a temperature at 25° C. over a period of 12 hours. During this time, proper oxygen supply was maintained by aerating the fermentor with an air-flow rate of 5.5 liters per minute. At this point, a sufficient quantity of cells was available to form an inoculum for the 150-liter fermentor. Thus, the contents of the 14-liter fermentor were aseptically transferred to the 150-liter fermentor which had previously been charged with 100 liters of a sterilized production medium, the particular composition of which is described in the following examples. Thereafter, the contents of the 150-liter fermentor were agitated at 250 rpm for a period of about 12 hours. During this time, the fermentor was aerated with an air-flow rate of 46 liters/minute. Dissolved oxygen concentration and pH were monitored continuously throughout the 12-hour period. Samples were drawn from the fermentor at the end of each hour and a measurement of dry cell weight was made. In addition, at the end of each hour, a 2.5 ml aliquot was withdrawn from the fermentor and treated as described in Procedure 2 above to separate the cells. The cells were then disrupted and assayed as described in Procedures 4 and 5 below.

4. Cell Disruption

Cell disruption was achieved in Procedures 2 and 3 above and in the examples below as follows:

0.2 ml of an enzyme solution and 0.4 ml of cell suspension were added to 1.4 ml of 0.05 M tris(hydroxymethyl)aminomethane (tris) buffer, pH 8.5, and $10^{-3}$ M (ethylenedinitrilo)tetraacetic acid, dipotassium salt ($K_2EDTA$). The aforementioned enzyme solution contained per ml of deionized water: 2.5 mg lysozyme, 1 mg bovine pancreatic deoxyribonuclease, and 1 mg bovine pancreatic ribonuclease. The amount of cell suspension was adjusted to give a final optical density of about 1.0, and the final volume was made to 2.0 ml with tris buffer. The suspension was shaken in a water bath at 37° C. for 20 minutes. The cell debris was removed by centrifugation at 27,000 xg in a refrigerated centrifuge, and the supernatant was assayed for enzyme activity as described in Procedure 5 below.

5. Assay of Creatinine Iminohydrolase

To determine the creatinine iminohydrolase activity described in the Examples, a L-glutamic dehydrogenase, "GDH", assay method was employed. In the GDH assay method, production of ammonia from creatinine, which represents the activity of a creatinine iminohydrolase enzyme preparation, is measured using NADPH (nicotinamide-adenine dinucleotide phosphate, reduced form) in a GDH-catalyzed reaction as follows:

Creatinine is hydrolyzed to ammonia via the unknown activity of a creatinine iminohydrolase sample, and the resultant ammonia reacts with the reagent α-ketoglutaric acid in the presence of GDH as catalyst to produce glutamic acid. The latter reaction catalyzed by GDH uses the NADPH oxidation reaction (NADPH- →NADP), the disappearance of the NADPH absorption peak at 340 nm providing the spectroscopically detectable means for monitoring the assay. That is, the rate of NADPH disappearance measures the rate of glutamic acid production which, in turn, measures the rate of ammonia production. The reaction mixture employed in the GDH assay method contained, in a total volume of one milliliter of 0.1 M N,N-bis(2-hydroxyethyl)glycine-KOH buffer solution having a pH of 7.6:0.4 mg (ethylenedinitrilo) tetraacetic acid, disodium salt ($Na_2$-EDTA), 1.6 mg α-ketoglutaric acid, 0.24 mg NADPH, 15 units GDH (ammonia-free), and 4.52 mg creatinine. One unit of GDH activity is defined as that amount of enzyme which catalyzes reduction of 1μ mole of α-ketoglutaric to glutamate per minute at pH 7.6 and 37° C. Reaction was initiated in the above-noted reaction mixture by addition of a small sample (about 2-10 milliunits) of the desired creatinine iminohydrolase enzyme preparation after equilibration of the reaction mixture at 37° C. Creatinine iminohydrolase activity was calculated by measuring the NADPH rate of disappearance at 340 nm (the molar extinction coefficient of NADPH at 340 nm being $6.22 \times 10^3$) in a spectrophotometer. One unit of enzyme activity was defined as that amount of enzyme necessary to catalyze the conversion of 1μ mole of creatinine to 1μ mole of ammonia per minute under the above-noted GDH assay reaction conditions.

cellular growth in each flask was measured and is reported in Table I as dry cell weight per liter of medium. As shown in the first column of Table I, the culture grew well in Tryp-Soy Broth, Micro Inoculum Broth and Medium No. 2. Next, flasks containing 25 ml of Medium No. 2 as a production medium were inoculated with 2 ml of suspension from each of the microbial growth media tested. As shown in Table I, good growth and excellent enzyme production in the production medium were observed in those flasks inoculated with the cultures obtained from Tryp-Soy Broth and Micro Inoculum Broth. Those flasks inoculated with the culture from Medium No. 2 gave good cell growth but did not give high levels of enzyme production. Those flasks inoculated with Sabouraud Dextrose Broth and Nutrient Broth gave poor results. The Sabouraud Dextrose Broth provided poor cell growth and little or no enzyme production. The Nutrient Broth although providing some enzyme production yielded poor cell growth.

TABLE I

| Microbial Growth Medium | Cellular Growth in Microbial Growth Medium g/liter | Cellular Growth in Production Medium g/liter | Creatinine Iminohydrolase Production U/liter |
|---|---|---|---|
| Tryp-Soy Broth as described in Procedure 1 above | 3.46 | 1.38 | 324 |
| Sabouraud Dextrose Broth tradename of Difco Laboratories (Detroit,MI) containing peptic casein hydrolysate and dextrose (glucose) | 0.47 | —[a] | —[a] |
| Nutrient Broth tradename of Difco Laboratories (Detroit,MI) containing beef protein hydrolysate and peptic casein hydrolysate | 0.81 | 0.87 | 104 |
| Micro Inoculum Broth tradename of Difco Laboratories (Detroit, MI) containing protease casein hydrolysate, yeast extract, glucose, $KH_2PO_4$, and sorbitan monooleate complex | 4.00 | 1.76 | 300 |
| Medium No. 2 (described above) | 2.65 | 1.19 | 100 |

[a]The growth and the enzyme production was below the detection limits of the assays of 0.1 g/liter and 20 U/liter, respectively.

EXAMPLE 1

Microbial Growth Medium

This example reports the results of tests to define useful microbial growth media for a fermentation process of the present invention. The process used in this example employs a variety of different microbial growth media as shown in Table I and Medium No. 2 described above as a production medium. Medium No. 2 does not represent an improved aqueous nutrient medium of the invention as it does not contain a vegetable or non-peptic milk protein hydrolysate. The procedure of the process used in this example was as follows:

Flasks containing 25 ml of each media tested were inoculated with a loopful of the culture that was grown on Medium No. 1 slants for 2 days at 30° C. The flasks were shaken at 200 rpm at 30° C. for 18 hours. The

EXAMPLE 2

Effect of Carbon Sources

Using Procedure 2 above for Small-scale Enzyme Production, several compounds, including acids, alcohols, and sugars, were tested to determine an optimum carbon source for the aqueous nutrient medium used as the production medium in Procedure 2. Each of the aqueous nutrient media tested in this example were identical to Medium No. 2 above except that the carbon source was replaced by the particular compound set forth as shown hereinafter in Table II. These aqueous nutrient media do not represent improved aqueous nutrient media of the invention, as they did not contain a vegetable or non-peptic casein protein hydrolysate. A series of aqueous media was tested for each different carbon source shown in Table II to determine the optimum concentration of each carbon source. Optimum concentration was determined on the basis of that concentration which produced the highest creatinine iminohydrolase activity. The series of media for each carbon source tested was compared to a control medium containing as the carbon source 1.0 wt% fumaric acid. Thus, dry cell weight and creatinine iminohydrolase activity for each carbon source tested in Table II was determined as a percentage relative to that of the fumaric acid control for that series. As shown in Table II, glycerol, sucrose, acetic acid, and glycine (an amino acid) did not support the growth of the culture or produce a detectable amount of enzyme. In the case of aspartic and glutamic acids (also amino acids) the culture grew well but these sources repressed enzyme synthesis. In contrast to the foregoing carbon sources, acceptable levels of microbial growth and enzyme production were obtained from those media employing as the carbon source either glucose or an indirect amino acid precursor such as lactic acid, malic acid, citric acid, or succinic acid. As further shown in Table II the direct amino acid precursor pyruvic acid supported good enzyme production although somewhat lower growth of the microorganism was obtained. Fumaric acid, a direct amino acid precursor and the control used in Table II, also yielded good enzyme production and good growth of the microorganism. α-Ketoglutaric acid appeared to provide best results as it provided good growth of the microorganism and produced more than twice as much enzyme as did the fumaric acid control. These results demonstrated that glucose and indirect amino acid precursors served as useful carbon sources, while direct amino acid precursors such as fumaric acid, α-ketoglutaric acid, and pyruvic acid served as even better carbon sources with α-ketoglutaric acid providing exceptional results.

TABLE II

Effect of Carbon Source

| Carbon Source | Optimum Concentration Wt. % | Dry Cell Wt. % of Control | Creatinine Iminohydrolase Activity % of Control |
|---|---|---|---|
| Fumaric Acid[a] | 1.0 | 100 | 100 |
| Glucose | 1.0 | 72 | 51 |
| Glycerol | 0.5 | 18 | — |
| Sucrose | 0.5 | 16 | — |
| Acetic Acid | 0.1 | 16 | — |
| Lactic Acid | 0.5 | 83 | 8 |
| Pyruvic Acid | 0.5 | 71 | 105 |
| Citric Acid | 1.0 | 76 | 71 |
| Succinic Acid | 1.0 | 60 | 49 |
| Malic Acid | 1.0 | 74 | 100 |
| α-Ketoglutaric Acid | 1.0 | 104 | 205 |
| Aspartic Acid | 1.0 | 96 | — |
| Glutamic Acid | 1.0 | 117 | — |
| Alanine | 1.0 | 64 | 35 |
| Glycine | 0.5 | 7 | — |

—Below the detection limit of creatinine iminohydrolase assay of 20 U/liter.
[a]Fumaric acid (1.0%) was used as control.

EXAMPLE 3

Effect of Fumaric Acid and Creatinine

The concentrations of fumaric acid (carbon source) and creatinine (nitrogen source) were tested in aqueous nutrient media employed as the production medium using Procedure 2 above for Small-scale Enzyme Production. These aqueous nutrient media do not represent improved aqueous nutrient media of the invention as they did not contain a vegetable or non-peptic casein protein hydrolysate. The concentrations of the fumaric acid and creatinine were varied simultaneously using an aqueous medium identical to that of Medium No. 2 above, except that the fumaric acid and creatinine concentrations were varied as indicated in Table III below. Table III below shows the optimum concentrations of fumaric acid as a carbon source to be 1.0% and that of creatinine to be 0.5%. In all other combinations tested, reduced growth and reduced enzyme yield were observed.

TABLE III

Effect of Fumaric Acid and Creatinine

| Concentration of Fumaric Acid Wt. % | Concentration of Creatinine Wt. % | Dry Cell Weight g/liter | Creatinine Iminohydrolase Activity U/liter |
|---|---|---|---|
| 1.0 | 0.0 | 1.08 | —[a] |
|  | 0.5 | 3.24 | 205 |
|  | 1.0 | 3.41 | 160 |
| 1.5 | 0.5 | 2.81 | 146 |
|  | 1.0 | 2.63 | 157 |
| 2.0 | 0.5 | 2.87 | 168 |
|  | 1.0 | 2.51 | 138 |

[a]Below the detection limit of the creatinine iminohydrolase assay of 10 U/liter.

EXAMPLE 4

Effect of Additional Nitrogen Source

In each of examples 2 and 3 noted above, the sole nitrogen source employed in the production medium of the Small-scale Enzyme Production process of Procedure 2 above was creatinine. In this example, the use of additional nitrogen sources, namely, a vegetable protein hydrolysate, Hy-Soy (a tradename for soy protein hydrolysate made by Scheffield Chemical, Union, N.J.) and a milk protein hydrolysate, Trypticase ® Peptone (a tryptic casein hydrolysate made by Bioquest (BBL), Cockeysville, Md.), were added to the production medium and evaluated in the Small-scale Enzyme Production process as described in Procedure 2 above at the concentration levels noted in Table IV below to determine their effects as additional nitrogen sources. Thus, these aqueous nutrient media represented improved aqueous nutrient media of the invention. The remainder of the production medium used in each of the tests conducted as reported in Table IV below was identical to Medium No. 2 above. As shown in Table IV below, in the case of Hy-Soy, best results were obtained at a concentration level of about 0.5 wt%. In the case of Trypticase ® Peptone, best results were obtained at a concentration level of 0.1 wt%. Although levels of Hy-Soy and Trypticase ® Peptone above 0.5 and 0.1 wt%, respectively, could be employed, enzyme repression began to occur at these higher levels.

TABLE IV

Effect of Additional Nitrogen Source

| Additional Nitrogen Source | Concentration of Additional Nitrogen Wt. % Source | Dry Cell Weight % of Control | Creatinine Iminohydrolase Acitivity % of Control |
|---|---|---|---|
| None[a] | — | 100 | 100 |
| Hy-Soy | 0.1 | 114 | 104 |
| Hy-Soy | 0.5 | 108 | 120 |
| Hy-Soy | 1.0 | 128 | 75 |
| Trypticase ® Peptone | 0.1 | 101 | 110 |
| Trypticase ® Peptone | 0.5 | 106 | 59 |
| Trypticase ® Peptone | 1.0 | 102 | 35 |

[a]Control - culture grown on Medium No. 2

EXAMPLE 5

Effect of Combination Carbon Source

In this example, a combination carbon source composed of both glucose and an amino acid precursor was investigated to determine its effect on the growth and enzyme production of the microorganism. The tests in this example were conducted using both the Small-scale Enzyme Production process of Procedure 2 above and the Large-scale Enzyme Production process of Procedure 3 above. In each case, the composition of the final production medium was identical to that of Medium No. 2 above, except that glucose concentrations, as shown in Table V below, were added. The results of Table V below show that while addition of glucose enhanced the growth of the culture only slightly, the combination of the glucose and amino acid precursor carbon source produced marked enhancement of enzyme production.

TABLE V

Effect of Combination Carbon Source - Glucose

| Conc. of Glucose Wt. % | Enzyme Production Procedure | Dry Cell Weight g/liter | Creatinine Iminohydrolase Activity U/liter | Creatinine Iminohydrolase Activity % of Control |
|---|---|---|---|---|
| 0.0[a] | No. 2 | 3.29 | 101 | 100 |
| 1.0 | No. 2 | 3.31 | 136 | 135 |
| 0.0[a] | No. 3 | 3.61 | 538 | 100 |
| 1.0 | No. 3 | 3.92 | 720 | 134 |

[a]Control - Culture grown on Medium No. 2.

EXAMPLE 6

Results of Medium Modifications on Large-Scale Enzyme Production

In this example the combined effect of the foregoing modifications to the production medium described in Examples 2-5 above was investigated using the Large-scale Enzyme Production process described in Procedure 3 above. In this example, the control production medium consisted of Medium No. 2 above. In the remaining tests of this example, modifications of Medium No. 2 were made as described hereinafter in Table VI. The only modification in Table VI not discussed previously in Examples 2-5 above was the replacement of the base KOH in Medium No. 2 with that of NaOH. This was done because it was found that improved enzyme production could be obtained by replacing the KOH with NaOH. In Table VI below, Media B, C and D, all representing improved aqueous nutrient media of the type employed in the present invention, produced markedly improved enzyme activity levels over that of control Medium A, identical to Medium No. 2 described above. In particular, Media C and D containing an additional nitrogen source as well as a combination carbon source produced significant increases in enzyme production. During the large-scale production processes run in this example, the kinetics of the fermentation process in the 150-liter fermentor were observed for each of Media B, C and D noted in Table VI below. For Medium B, it was observed that growth of the microorganism began almost immediately, increased exponentially, and then reached a plateau of 3.8 g/l in about 10 hours; enzyme production for Medium B which began after about a 4 hour lag increased exponentially approximately parallel to that of growth until a maximum level of enzyme production was obtained after about 10 hours. For Medium C below, growth of the microorganism increased exponentially during the first 3 hours into the fermentation process and reached a plateau of 4 g/l in about 10 hours. Enzyme production for Medium C began about 4.5 hours after initiation of the fermentation process and increased exponentially roughly in parallel to the growth. The maximum level of enzyme production for Medium C was obtained in about 11-13 hours after which the activity began to decrease. For Medium D, growth of the microorganism increased exponentially during the first 4 hours after which it plateaued at about 4 g/l. Enzyme production for Medium D began after about 5 hours and also increased exponentially roughly in parallel to the growth until a maximum level of enzyme production was achieved after about 11-13 hours.

TABLE VI

Effect of Medium Modifications On Large-Scale Enzyme Production

| Medium | Modification | Creatinine Iminohydrolase Activity U/liter | Creatinine Iminohydrolase Activity % of Control |
|---|---|---|---|
| A | None[a] | 295 | 100 |
| B | Neutralized with NaOH and 0.1% Trypticase ® Peptone | 538 | 182 |
| C | Neutralized with NaOH, 0.1% Trypticase ® Peptone, and 1.0% glucose | 720 | 244 |
| D | Neutralized with NaOH, 0.1% Trypticase ® Peptone, 1.0% glucose, and α-ketoglutaric acid in place of fumaric acid | 828 | 281 |

[a]Control - culture grown on Medium No. 2.

EXAMPLE 7

To demonstrate the increase in yield of creatinine iminohydrolase enzyme obtained from aerobic soil microorganisms grown in an improved aqueous nutrient medium of the present invention, two different aerobic creatinine iminohydrolase-producing microorganisms, namely *Brevibacterium divaricatum* ATCC 14020 (referred to in U.S. Pat. Nos. 4,087,329 and 4,134,793) and the urease-free creatinine iminohydrolase-producing microorganism ATCC 31546 described in Procedure 1 above, were grown in two different aqueous nutrient media. Specifically, each of these two different microorganisms were grown in identical quantities of a control nutrient medium having the composition described in Example 1 of U.S. Pat. No. 4,087,329 and as set forth hereinafter in Table VII. The procedure used for cultivation of these cultures was the same as that described in Example 6 of U.S. Pat. No. 4,087,329 as set forth hereinafter in Table VIII. Thereafter, the cells of each of the two microorganisms were harvested by centrifugation at 1500×g for 15 minutes in a refrigerated centrifuge. The cell pellet thus obtained from centrifuging 50 ml of fermentation broth was resuspended in 10 ml of 0.1 M potassium phosphate buffer pH 7.5 and was sonicated for 5 minutes to extract enzyme produced within the microbial cells. Cell debris was removed by centrifugation at 27000×g for 15 minutes in a refrigerated centrifuge. The resultant crude, unpurified enzyme-containing supernatants obtained from each of the two microorganisms were then assayed as described in Procedure 5 above to determine their creatinine iminohydrolase activity and thus obtain a quantitative evaluation of the yield of creatinine iminohydrolase from each microorganism. Thereafter, the foregoing procedure was repeated with each of the above-described microorganisms, except that this time each of the microorganisms was grown in identical quantities of an improved aqueous nutrient medium of the present invention having a composition identical to that of Medium D of Example 6 of the present specification. The yield of creatinine iminohydrolase, i.e., the creatinine iminohydrolase activity harvested from the two microorganisms grown in Medium D, was then quantified in the same manner as described above. The results are set below in Table IX. As shown in Table IX, the yield of creatinine iminohydrolase produced by each of these two different microorganisms was significantly increased by growing the microorganisms in an improved aqueous nutrient medium of the present invention.

TABLE VII

| Control Medium | |
| --- | --- |
| | Per Liter |
| Glucose | 20.0 g |
| Creatinine Hydrochloride | 5.0 g |
| K$_2$HPO$_4$ | 1.0 g |
| MgSO$_4$ . 7H$_2$O | 0.5 g |
| KCl | 0.5 g |
| Yeast Extract | 1.0 g |
| Adjust pH to 7.5 and make to 1 liter with distilled water. | |

TABLE VIII

| Cultivation Conditions | |
| --- | --- |
| Condition | Description |
| Volume of Medium | 25 ml in 250-ml Erlenmeyer flask |
| Temperature | 30° C. |
| Shaker Speed | 200 rpm |
| Duration | 24 hours |

TABLE IX

| Yield of Creatinine Iminohydrolase | | |
| --- | --- | --- |
| Microorganism | Medium | Creatinine Iminohydrolase Activity (% of Control)* |
| ATCC 14020 | Table VII Control Medium | 100 |
| ATCC 14020 | Medium D of Example 6 | 358 |
| ATCC 31546 | Table VII Control Medium | 100 |
| ATCC 21546 | Medium D of Example 6 | 300 |

*The absolute value of the creatinine iminohydrolase activity level of the crude unpurified supernatant obtained from each of the microorganisms grown in the Table VII control medium was arbitrarily assigned a value of 100. The creatinine iminohydrolase activity level of the unpurified supernatants obtained from each of the microorganisms grown in Medium D of Example 6 is then expressed in Table IX above as a percentage relative to the Table VII control medium.

The invention has been described in detail with particular reference to certain preferred embodiments thereof, but it will be understood that variations and modifications can be effected within the spirit and scope of the invention.

What is claimed is:

1. A fermentation process for production of creatinine iminohydrolase from an aerobic soil microorganism maintained on an aqueous maintenance medium containing creatinine under aerobic conditions at a pH of from about 5.0 to 10.0, said process comprising the steps of:
(a) transferring a fresh sample of said microorganism from said maintenance medium to a microbial growth medium having a pH of from about 5.0 to 10.0 to grow the microorganism, said growth medium comprising an aqueous nutrient medium, substantially free from creatinine, containing nutrients including a vegetable or non-peptic milk protein hydrolysate effective under aerobic conditions to grow said microorganism;
(b) transferring the microbial growth medium containing the growing microorganism obtained in step (a) to a production medium having a pH in the range of from about 5.0 to 10.0 to generate under aerobic conditions microorganism in which creatinine iminohydrolase production has been induced, said production medium representing an aqueous nutrient medium which comprises:
(i) a carbon source comprising glucose or an amino acid precursor representing an organic acid free from amino groups, or a mixture thereof,
(ii) a nitrogen source comprising creatinine,
(iii) trace nutrients, and
(iv) a buffer; and
(c) extracting urease-free creatinine iminohydrolase from said microorganism generated in step (b).

2. A fermentation process for production of creatinine iminohydrolase as defined in claim 1 wherein said production medium in step (b) contains:
(i) a carbon source comprising a direct amino acid precursor representing an organic acid free from amino groups,
(ii) a nitrogen source comprising creatinine and a vegetable protein hydrolysate or a non-peptic milk protein hydrolysate or a mixture of said vegetable protein hydrolysate and said non-peptic milk protein hydrolysate,
(iii) trace nutrients comprising water-soluble inorganic salts, and
(iv) a phosphorous-containing buffer.

3. A fermentation process for production of creatinine iminohydrolase as defined in either of claims 1 or 2 wherein said production medium in step (b) contains as said carbon source (i) a mixture of glucose and said amino acid precursor.

4. A fermentation process for production of urease-free creatinine iminohydrolase from the aerobic soil microorganism ATCC 31546 grown on an aqueous maintenance medium containing creatinine under aerobic conditions at a pH of from about 5.0 to 10.0, said process comprising the steps of:
(a) transferring a fresh sample of said microorganism from said maintenance medium to a microbial growth medium having a pH of from about 5.0 to 10.0 to grow said microorganism, said growth medium comprising an aqueous nutrient medium substantially free from creatinine, containing nutrients including a vegetable or non-peptic milk protein hydrolysate effective under aerobic conditions to grow said microorganism;
(b) transferring the microbial growth medium containing the growing microorganism obtained in step (a) to a production medium having a pH in the range of from about 5.0 to 10.0 to generate under aerobic conditions a microorganism in which creatinine iminohydrolase production has been induced, said production medium representing an aqueous nutrient medium which comprises:
(i) a carbon source comprising glucose and an amino acid precursor selected from the group consisting of fumaric acid, malic acid, α-ketoglutaric acid, and pyruvic acid, (ii) a nitrogen source comprising creatinine and a vegetable protein hydrolysate or a non-peptic milk protein hydrolysate or a mixture of said vegetable protein hydrolysate and said non-peptic milk protein hydrolysate, (iii) trace nutrients comprising yeast extract and a mixture of water-soluble inorganic salts, and (iv) a phosphate buffer; and (c) extracting urease-free creatinine iminohydrolase from said microorganism generated in step (b).

5. A fermentation process for production of urease-free creatinine iminohydrolase as defined in claim 4 wherein said process is carried out at a temperature in the range of from about 20° to 37° C. and wherein said carbon source comprises a weight ratio of glucose to amino acid precursor within the range of from 1:10 to 1:1.

6. A fermentation process for production of creatinine iminohydrolase as defined in claim 1 or 4 wherein said process is carried out using a production medium in step (b) having a pH adjusted to an initial value of from about 6.0 to 7.5.

7. A fermentation process for production of creatinine iminohydrolase as defined in claim 1 or 4 wherein said process is carried out using a production medium in step (b) containing an amount of NaOH or KOH sufficient to adjust the initial pH value of said production medium to a value within the range of from about 6.0 to 7.5.

8. A fermentation process for production of creatinine iminohydrolase as defined in either of claims 1 or 4 wherein step (a) is carried out in at least two stages comprising a first stage wherein said fresh sample is transferred to a first volume of said microbial growth medium to grow the microorganism and at least one additional stage wherein said growing microorganism from said first stage is transferred to a second, larger volume of said microbial growth medium to produce a larger volume of said growing microorganism for step (b).

9. An improved aqueous nutrient medium for growing under aerobic conditions a creatinine iminohydrolase-producing aerobic soil microorganism, said aqueous nutrient medium having a pH in the range of from about 5.0 to 10.0 and comprising:

(i) a carbon source comprising glucose or an amino acid precursor representing an organic acid free from amino groups, or a mixture thereof, (ii) a nitrogen source comprising creatinine and an enzyme-stimulating amount of a vegetable protein hydrolysate or a non-peptic milk protein hydrolysate or a mixture of said vegetable protein hydrolysate and a non-peptic milk protein hydrolysate, (iii) trace nutrients, and (iv) a buffer.

10. An improved aqueous nutrient medium as defined in claim 9 wherein said carbon source comprises a direct amino acid precursor.

11. An improved aqueous nutrient medium as defined in claim 9 wherein said carbon source comprises a mixture of glucose and said amino said precursor.

12. An improved aqueous nutrient medium for growing under aerobic conditions the aerobic soil microorganism ATCC 31546, said aqueous nutrient medium having a pH in the range of from about 5.0 to 10.0 and comprising:

(i) a carbon source comprising an amino acid precursor representing an organic acid free from amino groups, (ii) a nitrogen source comprising creatinine and an enzyme-stimulating amount of a vegetable protein hydrolysate or a non-peptic milk protein hydrolysate or a mixture of said vegetable protein hydrolysate and a non-peptic milk protein hydrolysate, (iii) trace nutrients comprising water-soluble inorganic salts, and (iv) a phosphorous-containing buffer.

13. An improved aqueous nutrient medium as defined in claim 12 wherein NaOH or KOH is present in said medium in an amount effective to adjust the pH of said medium to a value within the range of from about 6.0 to 7.5.

14. An improved aqueous nutrient medium as defined in claim 12 or 13 wherein said carbon source comprises glucose and an amino said precursor selected from the group consisting of fumaric acid, malic acid, α-ketoglutaric acid and pyruvic acid.

15. An improved aqueous nitrient medium as defined in claim 12 or 13 wherein said carbon source comprises a mixture of glucose and α-ketoglutaric acid in a weight ratio of from about 1:10 to 1:1.

16. An improved aqueous nutrient medium for growing under aerobic conditions the aerobic soil microorganism ATCC 31546, said aqueous nutrient medium having a pH in the range of from about 5.0 to 10.0 and comprising:

(i) a carbon source comprising an amino acid precursor representing an organic acid free from amino groups, (ii) a nitrogen source comprising creatinine and an enzyme-stimulating amount of a vegetable protein hydrolysate or a non-peptic milk protein hydrolysate or a mixture of said vegetable protein hydrolysate and a non-peptic milk protein hydrolysate, (iii) trace nutrients comprising yeast extract and a mixture of water-soluble inorganic salts, and (iv) a phosphate buffer.

17. An improved aqueous nutrient medium as defined in claim 16 wherein said medium also contains NaOH or KOH in an amount effective to adjust the pH of said medium to a value within the range of from about 6.0 to 7.5.

* * * * *